United States Patent [19]

Grollier et al.

[11] Patent Number: 4,488,564

[45] Date of Patent: Dec. 18, 1984

[54] OILY COMPOSITION INTENDED FOR THE TREATMENT OF KERATIN SUBSTANCES AND THE SKIN

[75] Inventors: Jean F. Grollier, Paris; Josiane Allec, Pierrefitte-sur-Seine, both of France

[73] Assignee: L'Oreal, Paris, France

[21] Appl. No.: 331,904

[22] Filed: Dec. 18, 1981

[30] Foreign Application Priority Data

Dec. 19, 1980 [LU] Luxembourg ............................ 83020

[51] Int. Cl.³ .......................... A45D 19/00; A61K 7/06
[52] U.S. Cl. ........................................... 132/7; 424/47; 424/70; 424/71; 424/72; 424/78; 424/80; 424/81
[58] Field of Search ................... 424/70, 71, 47; 132/7

[56] References Cited

U.S. PATENT DOCUMENTS

| | | | |
|---|---|---|---|
| 2,261,002 | 10/1941 | Ritter | 260/570 |
| 2,271,378 | 1/1942 | Searle | 167/22 |
| 2,273,780 | 2/1942 | Dittmar | 260/28 |
| 2,375,853 | 5/1945 | Kirby et al. | 260/583 |
| 2,388,614 | 11/1945 | Kirby et al. | 167/22 |
| 2,454,547 | 11/1948 | Bock et al. | 260/567.6 |
| 2,961,347 | 11/1960 | Floyd | 117/141 |
| 3,206,462 | 9/1965 | McCarty | 260/256.4 |
| 3,227,615 | 1/1966 | Kordon | 167/87.1 |
| 3,589,978 | 6/1971 | Kamal | 162/158 |
| 3,874,870 | 4/1975 | Green et al. | 71/67 |
| 3,929,990 | 12/1975 | Green et al. | 424/78 |
| 3,966,904 | 6/1976 | Green et al. | 424/78 |
| 4,001,432 | 1/1977 | Green et al. | 424/329 |
| 4,005,193 | 1/1977 | Green et al. | 424/168 |
| 4,025,617 | 5/1977 | Green et al. | 424/78 |
| 4,025,627 | 5/1977 | Green et al. | 424/248.4 |
| 4,025,653 | 5/1977 | Green et al. | 424/325 |
| 4,026,945 | 5/1977 | Green et al. | 260/567.6 |
| 4,027,020 | 5/1977 | Green et al. | 424/248.56 |
| 4,031,307 | 6/1977 | DeMartino et al. | 536/114 |
| 4,240,450 | 12/1980 | Grollier et al. | 424/70 |

FOREIGN PATENT DOCUMENTS

| | | | |
|---|---|---|---|
| 1086004 | 7/1954 | France | 424/70 |
| 1492597 | 7/1967 | France | 424/70 |
| 1526808 | 4/1968 | France | 424/70 |
| 1583363 | 10/1969 | France | 424/70 |
| 2077143 | 9/1971 | France . | |
| 2080759 | 11/1971 | France . | |
| 2190406 | 6/1972 | France . | |
| 2162025 | 7/1973 | France | 424/70 |
| 2189434 | 1/1974 | France | 424/326 |
| 2208644 | 6/1974 | France | 424/70 |
| 2225145 | 11/1974 | France | 424/70 |
| 2252403 | 6/1975 | France . | |
| 2252840 | 6/1975 | France | 424/70 |
| 2280361 | 2/1976 | France | 424/70 |
| 2336434 | 12/1976 | France | 424/70 |
| 2316271 | 1/1977 | France | 424/70 |
| 2320330 | 4/1977 | France . | |
| 2368508 | 5/1978 | France . | |
| 1338760 | 3/1975 | United Kingdom . | |
| 1401089 | 7/1975 | United Kingdom . | |
| 1563163 | 3/1980 | United Kingdom . | |
| 2062460 | 9/1980 | United Kingdom . | |
| 2063671 | 11/1980 | United Kingdom . | |
| 2051161 | 1/1981 | United Kingdom . | |
| 1604471 | 12/1981 | United Kingdom | 424/70 |
| 1604472 | 12/1981 | United Kingdom | 424/70 |
| 1604473 | 12/1981 | United Kingdom . | |

*Primary Examiner*—Dale R. Ore
*Attorney, Agent, or Firm*—Fleit, Jacobson, Cohn & Price

[57] ABSTRACT

The specification discloses a foamable oily composition consisting of a single liquid phase, which is intended for the treatment of keratin substances, especially the hair and the skin, which contains at least one oily compound which is liquid at ambient temperature, an oil-soluble surface-active component, a cationic product and a small amount of water.

16 Claims, No Drawings

OILY COMPOSITION INTENDED FOR THE TREATMENT OF KERATIN SUBSTANCES AND THE SKIN

The present invention relates to oily compositions intended for the treatment of keratin substances and in particular for the treatment of human hair and the skin.

Oils and mixtures of oils have been used for many centuries for the care of the head of hair. These compositions have been recommended in particular if the hair has been dried out or sensitised, whether by external agents such as sunlight or seawater, or by treatments such as colouring, bleaching or perming.

However, the oils frequently require a long application time, as much as several hours in some instances, and this is rather incompatible with modern life. Moreover, they need to be removed by a shampoo, with the result that they ultimately make only a small improvement to the cosmetic properties such as the softness to the touch and the shine; furthermore the hair lacks hold. The use of oil-based products for the care of the hair is thus considerably less widespread than in the past.

Cationic compounds having a high affinity for keratin have also been used for a few years in the treatment of hair which has undergone natural or chemical attack, particularly if this keratin has been degraded.

These cationic compounds generally contain a nitrogen atom joined to one or more fatty chains and are optionally quaternised; they can also be polymers of the polyamine, polyaminoamide or quaternary polyammonium type, the amine or ammonium groups forming part of the polymer chain or being joined thereto.

The use of this type of material for the treatment of keratin substances, and in particular human hair and the skin, generally results in considerable improvement in the cosmetic properties and in particular in the comb-out of wet hair.

We have now discovered, according to the present invention, that it is possible to combine the cosmetic effects of cationic products and of oils by combining them in one and the same composition. A combination of this kind is particularly surprising in view of the fact that it is known that the incorporation of cationic products into oils presents substantial difficulties and has not been possible hitherto under satisfactory conditions. In fact, in certain cases, it is impossible to introduce the cationic product into the oil because it is insoluble or because the cationic product cannot be obtained in an anhydrous form. In other cases, where it is possible to introduce these cationic products, their effectiveness is very low because their ability to attach themselves to the hair is inhibited by the oily medium.

We have discovered a homogeneous composition which is liquid at ambient temperature, which is intended to be used for the treatment of keratin substances, and in particular human hair and the skin, and which makes it possible not only to use cationic products in an oily composition, but also to attach them to the hair or the skin so as to obtain, in combination with the oils, the desired cosmetic properties, in particular as regards the softness to the touch, the combing-out of wet or dry hair, and the shine; when applied to the skin, this composition, whilst being cleansing, does not have a drying-out effect and imparts softness.

The present invention thus provides a foaming or foamable oily composition consisting of a single liquid phase, which is intended for the treatment of keratin substances, and in particular of human hair and the skin, and which is based on an oily compound, a cationic derivative and an oil-soluble surface-active agent, as well as a process for the treatment of keratin substances using a composition of this type.

The foaming oily composition which consists of a single liquid phase, intended for the treatment of keratin substances, and in particular of human hair and the skin, according to the invention, is essentially characterised in that it consists of at least one oily compound which is liquid at ambient temperature (a temperature not exceeding 25° C.), an oil-soluble surface-active component, a cationic product and a small amount of water.

Preferably, the composition contains 5 to 85% of the oily compound, 15 to 95% of the oil-soluble surface-active component, 0.05 to 10% of cationic product and 0.1 to 5% of water. This single liquid phase composition has the advantage of spreading easily over the head of hair or over the skin, of forming a copious foam and of being easy to remove with water.

The oily compound which is liquid at ambient temperature can be, for example, a mineral, animal, vegetable or synthetic oil, a triglyceride of a synthetic fatty acid, a fatty alcohol or a fatty acid ester, used singly or in a mixture. Fatty means a group containing 8 and more carbon atoms.

Vaseline oil (liquid petrolatum) may be mentioned more particularly amongst the mineral oils.

Suitable animal oils include whale oil, seal oil, menhaden oil, halibut-liver oil, cod-liver oil, tuna oil, tallow oil, bovine oil, caballine oil, ovine oil, mink oil and otter oil.

Suitable vegetable oils include almond oil, peanut oil, wheatgerm oil, linseed oil, apricot kernel oil, nut oil, palm oil, pistachio oil, sesame oil, poppy oil, pine oil, castor oil, soya oil, avocado oil, safflower oil, coconut oil, hazel nut oil, olive oil, grapeseed oil, sunflower oil, colza oil, cade oil, maize germ oil, peach kernel oil, coffee bean oil and jojoba oil.

The triglycerides of synthetic fatty acids are, in particular, triglycerides of caprylic-capric acid and the triglycerides of fatty acids having 6 to 12 carbon atoms.

Suitable fatty alcohols can be unsaturated alcohol such as, oleyl alcohol, or saturated alcohols such as 2-octyldodecanol.

Suitable fatty acid esters include the isopropyl esters of myristic acid, palmitic acid and stearic acid.

The oily compound used according to the invention can optionally be oxyethyleneated.

The oil-soluble surface-active component may be an anionic surface-active agent, the acid group of which has been neutralised so as to make the said surface-active agent soluble in oil, and to which a non-ionic surface-active agent and/or an alkanolamide has optionally been added.

The oil-soluble surface-active agents which are particularly preferred for use in this invention include sulphated alkanols, sulphonated alkyl-benzenes, carboxylated alkyl polyglycol ethers and carboxylated alkylphenol polyglycol ethers, sulphated alkyl polyglycol ethers and sulphated alkylphenol polyglycol ethers, used singly or in a mixture and neutralised by an amine or a mixture of amines, optionally in the presence of one or more non-ionic surface-active agents.

The sulphated alkanols used according to the invention are, in particular, sulphated, saturated or unsaturated straight-chain or branched-chain alkanols containing 8 to 22 carbon atoms and preferably 12 to 16 carbon atoms. Suitable alkanols for such sulphated alkanols include decyl alcohol, lauryl alcohol, myristyl alcohol, cetyl alcohol, stearyl alcohol, oleyl alcohol and also alcohols obtained from oils of fats of natural origin, such as $C_{12}-C_{14}$ alcohols, oleyl-cetyl alcohol and $C_{12}-C_{18}$ fatty alcohols.

Typical sulphonated alkylbenzenes contain a straight-chain alkyl residue having 10 to 13 carbon atoms.

The sulphated alkyl polyglycol ethers are generally addition products of the abovementioned alkanols with 1 to 8 mols of ethylene oxide and preferably 1.5 to 3 mols of ethylene oxide.

The sulphated alkylphenol polyglycol ethers contain a straight-chain or branched-chain alkyl residue containing from 7 to 12 carbon atoms and 5 to 10 mols of ethylene oxide per molecule.

The carboxylated alkyl polyglycol ethers more particularly used comprise an alkyl radical of 12 to 18 carbon atoms and 2 to 20 moles of ethylene oxide units. The carboxylated alkylphenol polyglycol ethers usually comprise an alkyl radical of 7 to 12 carbon atoms and 2 to 20 moles of ethylene oxide units.

The amines used in the neutralisation of the acid groups of the anionic surface-active agent may be amines or alkanolamines. There may be mentioned, more particularly, monoalkylamines and polyalkylamines such as methylamine, ethylamine, diethylamine, propylamine, isopropylamine, butylamine and hexylamine, monoalkanolamines and polyalkanolamines such as ethanolamine, diethanolamine, triethanolamine, propanolamine and mono-, di- or tri-isopropanolamine, and mixed alkanolalkylamines such as dimethylaminoethanol, diethylaminoethanol, 2-amino-2-methylpropane-1,3-diol, aminomethylpropanol, N,N-dimethylisopropanolamine, N-propylethanolamine, N-propyldiethanolamine, N,N-diethylaminoethoxyethanol, monobutylethanolamine, tert.-butylethanolamine and tert.-butyldiethanolamine, used singly or in a mixture.

The non-ionic surface-active agents are preferably alkyl polyglycol ethers originating from straight-chain or branched-chain alkanols having 10 to 22 carbon atoms and preferably 10 to 16 carbon atoms and containing 1 to 8 mols of ethylene oxide units or alkylphenol polyglycol ethers having a straight-chain or branched-chain alkyl radical containing 7 to 12 carbon atoms and oxyethyleneated with 5 to 10 mols of ethylene oxide. Particularly preferred oxyethyleneated alkanols are decyl alcohol, lauryl alcohol, myristyl alcohol, cetyl alcohol, stearyl alcohol, oleyl alcohol, fatty alcohols of natural origin having 12 to 14 carbon atoms, oleyl-cetyl alcohol and fatty alcohols having 12 to 18 carbon atoms, oxyethyleneated with 1 to 8 mols of ethylene oxide.

Mixtures of surface-active agents which are more particularly preferred according to the invention are as follows:

(1) 40 to 50% by weight of oxyethyleneated fatty alcohols having 10 to 18 carbon atoms and preferably 12 to 14 carbon atoms, with 25 to 50% by weight, and preferably 30 to 40% by weight, of ethylene oxide;

(2) 25 to 35% by weight of salt of sulphated oxyethyleneated fatty alcohols mentioned under (1), salified with one or more aliphatic amines or with alkanolamines having 1 to 6 carbon atoms, more particularly isopropanol-amine;

(3) 10 to 20% by weight of alkanolamides preferably the diethanolamides of fatty acids having 10 to 18 carbon atoms; and (4) 5 to 15% by weight of sulphates or hydrochlorides of aliphatic amines or of alkanolamines having 1 to 6 carbon atoms, in particular isopropanolamine.

The alkanolamides of fatty acids are more particularly the monoethanolamide, diethanolamide, propanolamide and isopropanolamide of capric acid, undecylic acid, lauric acid, myristic acid, palmitic acid, stearic acid or oleic acid or mixtures of fatty acids having chains containing 10 to 18 carbon atoms, such as are obtained from fats and oils of natural origin.

Examples of the amine or alkanolamine salts which can be used include ethylamine sulphate, propylamine hydrochloride, isopropylamine sulphate, butylamine sulphate, hexylamine hydrochloride, hexylamine sulphate, monoethanolamine hydrochloride, diethanolamine sulphate, triethanolamine sulphate and propanolamine hydrochloride.

The compositions which are more particularly preferred are those based on sulphated lauryl alcohol oxyethyleneated with 2 to 5 moles of ethylene oxide, with a non-ionic surface-active agent, neutralised with an amine.

The cationic polymers used in the compositions according to the invention suitably have a molecular weight of 500 to 2,000,000 and are described more particularly in French Specifications Nos. 2,077,143, 1,492,597, 2,162,025, 2,280,361, 2,252,840, 2,368,508, 1,583,363, 2,080,759, 2,190,406, 2,320,330, 2,270,846, 2,316,271, 2,336,434 and 2,189,434; and U.S. Pat. Nos. 3,589,978, 4,031,307, 3,227,615, 2,961,347, 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020, the disclosure of all of which is hereby incorporated by reference.

Suitable polymers which can be used according to the invention are, in particular:

(1°) Vinylpyrrolidone/dialkylaminoalkyl acrylate or methacrylate copolymers (quaternised or non-quaternised) such as those sold under the name Gafquat by the Gaf Corp, such as "copolymer 845" and "Gafquat '34 or 735", described in greater detail, in particular, in French Pat. No. 2,077,143.

(2°) Cellulose ether derivatives containing quaternary ammonium groups, such as those described in French Pat. No. 1,492,597, and in particular the polymers sold under the name JR, such as JR 125, JR 400 and JR 30M, and the name LR, such as LR 400 and LR 30M, by the Union Carbide Corp, and cationic cellulose derivatives such as CELQUAT L 200 and CELQUAT L 50, sold by National Starch.

(3°) Cationic polysaccharides such as described in U.S. Pat. Nos. 3,589,978 and 4,031,307 and in particular Jaguar C 13 S sold by Meyhall.

(4°) Cationic polymers chosen from:

(a) polymers containing units of the formula: —A—Z—A—Z—, in which A denotes a radical containing two amine groups, preferably $$-N\phantom{xxx}\phantom{xxx}-$$

and Z denotes the symbol B or B'; B and B', which are identical or different, denote a divalent radical which is a straight-chain or branched-chain alkylene radical which contains up to 7 consecutive carbon atoms in the main chain, is unsubstituted or substituted by one or more hydroxyl groups and can also contain chain oxygen, nitrogen or sulphur atoms and 1 to 3 aromatic and/or heterocyclic rings, the oxygen, nitrogen and sulphur atoms being present in the form of ether or thioether, sulphoxide, sulphone, sulphonium, amine, alkyl-amine, alkenylamine, benzylamine, amine oxide, quaternary ammonium, amide, imide, alcohol, ester and/or urethane groups; these polymers and the process for their preparation are described in French Pat. No. 2,162,025;

(b) polymers containing units of the formula: $-A-Z_1-A-Z_1-$, in which A denotes a radical containing two amine groups, preferably

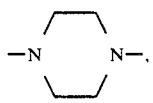

and $Z_1$ denotes the symbol $B_1$ or $B'_1$ such that at least one $Z_1$ denotes the symbol $B'_1$; $B_1$ denotes a divalent radical which is a straight-chain or branched-chain alkylene or hydroxyalkylene radical having up to 7 consecutive carbon atoms in the main chain, and $B'_1$ is a divalent radical which is a straight-chain or branched-chain alkylene radical which has up to 7 consecutive carbon atoms in the main chain, is unsubstituted or substituted by one or more hydroxyl radicals and containing one or more chain nitrogen atoms, the nitrogen atoms being substituted by an alkyl chain optionally containing a chain oxygen atom and containing one or more hydroxyl groups; these polymers and the process for their preparation are described in French Pat. No. 2,280,361; and (c) the quaternary ammonium salts and the oxidation products of the polymers of the formulae indicated above under (a) and (b).

(5°) Optionally alkylated, crosslinked polyaminoamides chosen from at least one water-soluble crosslinked polymer obtained by crosslinking a polyaminoamide (A) prepared by the polycondensation of an acidic compound with a polyamine. The acidic compound may be: (i) an organic dicarboxylic acid, (ii) an aliphatic monocarboxylic or dicarboxylic acid with an ethylenic double bond, (iii) an ester of the abovementioned acids, preferably an ester with an alkanol having from 1 to 6 carbon atoms, and (iv) mixtures of these products. The polyamine is a bis-primary, mono-secondary or bis-secondary polyalkylene-polyamine. Up to 40 mol % of this polyamine can be replaced by a bis-primary diamine, preferably ethylenediamine, or by a bis-secondary diamine, preferably piperazine, and up to 20 mol % can be replaced by hexamethylenediamine. The crosslinking is effected by means of a crosslinking agent (B) which may be an epihalogenohydrin, diepoxide, dianhydride, unsaturated anhydride or bis-unsaturated derivative; the crosslinking is characterised in that it is effected by means of 0.025 to 0.35 mol of crosslinking agent per amine group of the polyaminoamide (A), and generally by means of 0.025 to about 0.2 and in particular 0.025 to about 0.1 mol of crosslinking agent per amine group of the polyaminoamide (A). These polymers and their preparation are described in greater detail in French Pat. No. 2,252,840.

These crosslinked polymers are soluble in water at a concentration of 10% without gel formation, and the viscosity of a 10% strength solution in water at 25° C. is at least 3 centipoises and usually 3 to 200 centipoises.

The crosslinked and optionally alkylated polyaminoamides do not contain a reactive group, do not have alkylating properties and are chemically stable.

The polyaminoamides (A) themselves can also be used according to the invention.

(6°) The water-soluble crosslinked polyaminoamides obtained by crosslinking a polyaminoamide (A) described above, by means of a crosslinking agent chosen from:

(I) compounds which are (1) bis-halogenohydrins, (2) bis-azetidinium compounds, (3) bis-halogenoacyldiamines or (4) bis-(alkyl halides);

(II) the oligomers obtained by reacting a compound (a) chosen from (1) bis-halogenohydrins, (2) bis-azetidinium compounds, (3) bis-halogenoacyldiamines, (4) bis-(alkyl halides), (5) epihalogenohydrins, (6) diepoxides and (7) bis-unsaturated derivatives, with a compound (b) which is a difunctional compound which is reactive towards the compound (a); and (III) the quaternisation products of a compound chosen from the compounds (a) and the oligomers (II) and containing one or more tertiary amine groups which can be totally or partially alkylated with an "alkylating agent" (c) which is preferably methyl or ethyl chloride, bromide, iodide, sulphate, mesylate or tosylate, benzyl chloride or bromide, ethylene oxide, propylene oxide or glycidol. The crosslinking is suitably effected by means of 0.025 to 0.35 mol, in particular 0.025 to 0.2 mol, especially 0.025 to 0.1 mol of crosslinking agent per amine group of the polyaminoamide.

These crosslinking agents and these polymers, and also the process for their preparation, are described in French Patent Application No. 2,368,508.

(7°) Polyaminoamide derivatives resulting from the condensation of polyalkylene-polyamines with polycarboxylic acids, followed by alkylation with difunctional agents. Examples which may be mentioned are the adipic acid/dialkylaminohydroxyalkyl-dialkylenetriamine polymers in which the alkyl radical contains 1 to 4 carbon atoms and preferably denotes methyl, ethyl or propyl, and which are described in French Pat. No. 1,583,363.

Amongst these derivatives, there may be mentioned the adipic acid/dimethylaminohydroxypropyl-diethylenetriamine polymers sold under the name Cartaretine F, $F_4$ or $F_8$ by SANDOZ.

(8°) Polymers obtained by reacting a polyalkylene-polyamine containing two primary amine groups and at least one secondary amine group, with a carboxylic acid which is diglycolic acid or a saturated aliphatic dicarboxylic acid having 3 to 8 carbon atoms, the molar ratio of the polyalkylene-polyamine to the dicarboxylic acid being 0.8:1 to 1.4:1, and the resulting polyamide being reacted with epichlorohydrin in a molar ratio epichlorohydrin to the secondary amine groups of the polyamide of 0.5:1 to 1.8:1; these polymers are mentioned in U.S. Pat. Nos. 3,227,615 and 2,961,347.

Such polymers include those sold under the name HERCOSETT 57 by Hercules Incorporated which have a viscosity, at 25° C., of 30 cps as a 10% aqueous solution, and those sold under the name PD 170 or DELSETTE 101 by Hercules, in the case of the adipic acid/epoxypropyl-diethylenetriamine copolymer.

(9°) Cyclic polymers having a molecular weight of 20,000 to 3,000,000, such as the homopolymers containing, as the main constituent of the chain, units corresponding to the formula (II) or (II'):

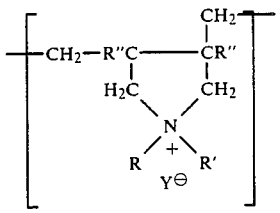

(II)

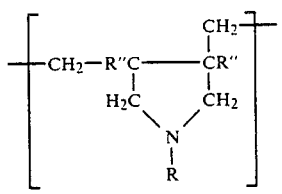

(II')

in which R" denotes hydrogen or methyl, R and R' independently denote an alkyl group having from 1 to 22 carbon atoms, a hydroxyalkyl group in which the alkyl group preferably has 1 to 5 carbon atoms, or a lower (e.g. $C_1$-$C_6$) amidoalkyl group, or R and R' denote together, with the nitrogen atom to which they are attached, a heterocyclic group such as piperidinyl or morpholinyl, and $Y^-$ is an anion such as bromide, chloride, acetate, borate, citrate, tartrate, bisulphate, bisulphite, sulphate or phosphate, and also the copolymers containing units of the formula II or II' and, preferably, acrylamide derivatives or diacetoneacrylamide derivatives.

Amongst such quaternary ammonium polymers, there may be mentioned the dimethyldiallylammonium chloride homopolymer sold under the name MERQUAT 100 having a molecular weight of less than 100,000, and the dimethyldiallylammonium chloride/acrylamide copolymer having a molecular weight of more than 500,000 sold under the name MERQUAT 550 by MERCK.

These polymers are described in French Pat. No. 2,080,759 and its Certificate of Addition No. 2,190,406.

(10°) The quaternary polyammonium compounds containing repeat units of the formula:

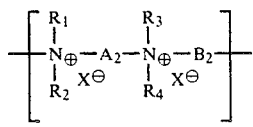

in which $R_1$ and $R_2$, and $R_3$ and $R_4$, which are identical or different, represent an aliphatic, alicyclic or arylaliphatic radical containing at most 20 carbon atoms, or a lower hydroxyaliphatic radical, or alternatively $R_1$ and $R_2$, and $R_3$ and $R_4$, together or separately form, with the nitrogen atoms to which they are attached, a heterocyclic ring optionally containing a second hetero-atom other than nitrogen, or alternatively $R_1$, $R_2$, $R_3$ and $R_4$ represent a group:

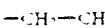

in which $R'_3$ denotes hydrogen or lower alkyl and $R'_4$ denotes one of the following groups: —CN, $$-\overset{O}{\underset{\|}{C}}-OR'_5, \quad -\overset{O}{\underset{\|}{C}}-R'_5, \quad -\overset{O}{\underset{\|}{C}}-N$$

$$-\overset{}{\underset{}{}}-O-R \cdot -O \quad \text{and} \quad -C-NH-R \cdot -O.$$

$R'_5$ denoting lower alkyl, $R'_6$ denoting hydrogen or lower alkyl, $R'_7$ denoting alkylene and D denoting a quaternary ammonium group. $A_2$ and $B_2$ independently represent polymethylene groups containing from 2 to 20 carbon atoms, which can be linear or branched and saturated or unsaturated and which can contain, inserted in the main chain, one or more aromatic rings such as the group:

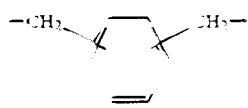

or one or more groups:

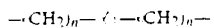

$Y_1$ denoting O, S, SO, $SO_2$, —S—S—

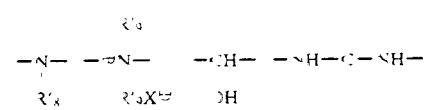

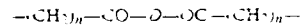

with $X^-$ denoting an anion derived from a mineral or organic acid, n being 2 or 3, $R'_8$ denoting hydrogen or lower alkyl and $R'_9$ denoting lower alkyl, or alternatively $A_2$ and $R_1$ and $R_3$ form a piperazine ring with the two nitrogen atoms to which they are attached; moreover, if A denotes a linear or branched, saturated or unsaturated alkylene or hydroxyalkylene radical, B can also denote a group:

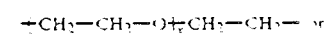

in which D denotes:

(a) a glycol radical of the formula —O—Z—O— in which Z denotes a linear or branched hydrocarbon radical or a group corresponding to the formulae:

—CH₂—CH₂—O—CH₂—CH₂— or

-continued

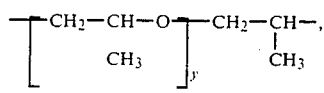

in which x and y independently denote an integer from 1 to 4, in any given compound, or any number from 1 to 4, representing an average value in a mixture of compounds;

(b) a bis-secondary diamine radical such as a piperazine derivative of the formula:

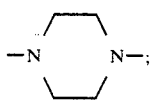

(c) a bis-primary diamine radical of the formula:

—NH—Y—NH— in which Y denotes a linear or branched hydrocarbon radical or the divalent radical

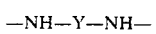

or (d) a ureylene group of the formula —NH—CO—NH—; and $X^-$ is an anion such as chloride or bromide.

These polymers generally have a molecular weight of 1,000 to 100,000.

Polymers of this type are described, in particular, in French Pat. Nos. 2,320,330 and 2,270,846, French Application Nos. 2,316,271, 2,336,434 and 2,413,907, and U.S. Pat. Nos. 2,273,780, 2,375,853, 2,388,614, 2,454,547, 3,206,462, 2,261,002 and 2,271,378.

Other polymers of this type are described in U.S. Pat. Nos. 3,874,870, 4,001,432, 3,929,990, 3,966,904, 4,005,193, 4,025,617, 4,025,627, 4,025,653, 4,026,945 and 4,027,020.

(11°) Homopolymers or copolymers derived from acrylic or methacrylic acid and containing the following unit:

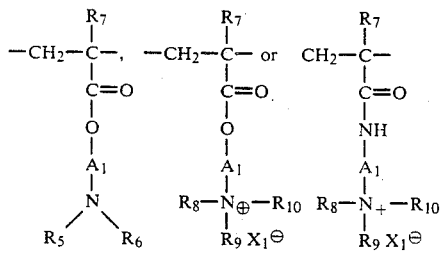

in which $R_7$ is H or $CH_3$, $A_1$ is a linear or branched alkyl group having up to 6 carbon atoms or a hydroxyalkyl group having 1 to 4 carbon atoms, $R_8$, $R_9$ and $R_{10}$, which are identical or different, represent an alkyl group having 1 to 18 carbon atoms or a benzyl group, $R_5$ and $R_6$ independently represent H or alkyl having 1 to 6 carbon atoms, and $X_1$ denotes halogen, such as chlorine or bromine, or methosulphate.

The comonomer or comonomers which can be used include: acrylamide, methacrylamide, diacetoneacrylamide, acrylamide and methacrylamide substituted on the nitrogen by lower alkyls, alkyl esters of acrylic and methacrylic acids, vinylpyrrolidone and vinyl esters.

Examples which may be mentioned are:

the acrylamide/beta-methacryloyloxyethyltrimethylammonium methosulphate copolymer sold under the names Reten 205, 210, 220 and 240 by Hercules, the ethyl methacrylate/oleyl methacrylate/betamethacryloyloxyethyldiethylmethylammonium methosulphate copolymers listed under the name Quaternium 38 in the Cosmetic Ingredient Dictionary, the ethyl methacrylate/abietyl methacrylate/betamethacryloyloxyethyldiethylmethylammonium methosulphate copolymer listed under the name Quaternium 37 in the Cosmetic Ingredient Dictionary, the beta-methacryloyloxyethyltrimethylammonium bromide polymer listed under the name Quaternium 49 in the Cosmetic Ingredient Dictionary, the beta-methacryloyloxyethyltrimethylammonium methosulphate/beta-methacryloyloxyethylstearyldimethylammonium methosulphate copolymer listed under the name Quaternium 42 in the Cosmetic Ingredient Dictionary, the aminoethylacryloyl phosphate/acrylate copolymer sold under the name Catrex by National Starch and having a viscosity of 700 cps at 25° C. in an 18% strength aqueous solution, and the crosslinked, graft cationic copolymers having a molecular weight of 10,000 to 1,000,000 and preferably of 15,000 to 500,000 and resulting from the copolymerisation of:

(a) at least one cosmetic monomer,
(b) dimethylaminoethyl methacrylate,
(c) polyethylene glycol and
(d) a polyunsaturated crosslinking agent, these copolymers being described in French Pat. No. 2,189,434.

The crosslinking agent is selected from:

ethylene glycol dimethacrylate, diallyl phthalates, divinylbenzenes, tetraallyloxyethane and polyallylsucroses having from 2 to 5 allyl groups per mol of sucrose.

The cosmetic monomer can be of a very varied type, for example a vinyl ester of an acid having from 2 to 18 carbon atoms, an allyl or methallyl ester of an acid having from 2 to 18 carbon atoms, an acrylate or methacrylate of a saturated alcohol having from 1 to 18 carbon atoms, an alkylvinyl ether, the alkyl radical of which contains from 2 to 18 carbon atoms, an olefine having from 4 to 18 carbon atoms, a vinyl heterocyclic derivative, a dialkyl or N,N-dialkylaminoalkyl maleate, the alkyl radicals of which have from 1 to 3 carbon atoms, or an anhydride of an unsaturated acid.

(12°) Quaternary polymers of vinylpyrrolidone and of vinylimidazole, such as Luviquat FC 905 sold by B.A.S.F.

Other cationic polymers which can be used are polyalkyleneimines, in particular polyethyleneimines, polymers containing vinylpyridine units or vinylpyridinium units in the chain, condensates of polyamines and of epichlorohydrin, quaternary polyureylenes, and chitin derivatives.

The cationic polymers which are preferred according to the invention are those belonging to families (9) and (10).

The cationic products, apart from the above-mentioned polymers, which can be used in the compositions according to the invention are fatty amine salts such as alkylamine acetates, quaternary ammonium salts such as alkyldimethylbenzylammonium, alkyltrimethylammonium, alkyldimethylhydroxyethylammonium and dimethyldistearylammonium chlorides and bromides, in which the alkyl radicals preferably have 1 to 22 carbon atoms, quaternary gluconamide halides such as described in U.S. Pat. No. 3,766,267, cationic protein hydrolysates, quaternary halides of mink oil amide, such as described in U.S. Pat. No. 4,012,398, quaternary derivatives of dialkylaminopropylamide fatty halogenoalkanoate, such as described in U.S. Pat. No. 4,038,294, quaternary ammonium derivatives of lanoline fatty acids, such as described in U.S. Pat. No. 4,069,347, alkylpyridinium salts and imidazoline derivatives.

The compositions which are particularly preferred according to the invention contain 30 to 100% of vaseline oil and 0 to 70% of vegetable oil as regards the oily compound.

The compositions according to the invention can also contain products normally used in the treatment of keratin substances and in particular in the treatment of the hair and the skin, such as solvents, such as lower alcohols or glycols, preservatives, antioxidants, dyestuffs, perfumes, thickeners, opacifying agents and agents for imparting pearlescence.

The composition can also be presented in the form of aerosols, containing a propellant gas conventionally used in cosmetics.

The process for the treatment of keratin substances, in particular human hair and the skin, consists essentially in applying the composition to the said substances, in emulsifying it after an application time of, say, 5 to 30 minutes, and in rinsing.

The compositions according to the invention can be used, in particular, as shampoos or as rinse-off products to be applied before or after shampooing, colouring, bleaching or perming, or as bath foams or "shower gels".

When used as a shampoo, the product is applied to dirty and, preferably, dry hair. After an application time of at least 5 minutes, the product is emulsified and then rinsed off. The composition is usually applied again in order to carry out a second shampooing stage. Approximately 30 to 40 ml of the composition according to the invention are suitable for this purpose.

When used as a rinse-off product, the product is applied to the hair and left for at least 5 minutes, and then rinsed off. In this case, generally approximately 15 to 30 ml of the composition according to the invention, and preferably 15 to 25 ml, are used.

The following Examples further illustrate the present invention.

EXAMPLE 1

The following composition is prepared:

| | |
|---|---|
| Texapon WW 99 | 15 g |
| Vaseline oil | 25 g |
| Polymer P1 (in 60% strength aqueous solution) | 3 g (1.8 g of active ingredient) |
| Perfume | |
| Antioxidant | |
| Olive oil q.s.p. | 100 g |

20 ml of this composition are applied to wet clean hair after shampooing. After an application time of 10 minutes, the hair is rinsed with water. It is found that the hair is easy to comb out and soft to the touch in the wet state, and these properties of softness and ease of comb-out are retained in the dry state.

EXAMPLE 2

The following composition is prepared:

| | |
|---|---|
| Texapon WW 99 | 7 g |
| Vaseline oil | 15 g |
| Polymer P1 in 60% strength aqueous solution | 7 g (3.4 g of active ingredient) |
| Perfume | |
| Antioxidant | |
| Preservative | |
| Peanut oil q.s.p. | 100 g |

The procedure described in Example 1 is followed and similar results are found.

EXAMPLE 3

The following composition is prepared:

| | |
|---|---|
| Texapon WW 99 | 10 g |
| Vaseline oil | 15 g |
| Polymer P1 in 60% strength aqueous solution | 7 g (3.4 g of active ingredient) |
| Dyestuff | |
| Antioxidant | |
| UV filter | |
| Colza oil q.s.p. | 100 g |

This composition is applied to dry dirty hair. After an application time of 5 minutes, it is emulsified. The formation of a foam which is soft to the touch is observed. After rinsing, the composition is applied to the hair again in order to carry out the second shampooing stage. After rinsing, the hair is soft to the touch and easy to comb out.

In this composition, the polymer P1 can be replaced by one of the following products:

| | | |
|---|---|---|
| (a) | Merquat 100 in 40% strength aqueous solution | 5 g (0.6 g of active ingredient) |
| (b) | Polymer P2 in 30% strength aqueous solution | 2 g (0.3 g of active ingredient) |
| (c) | Polymer P3 in 20% strength aqueous solution | .75 g (0.15 g of active ingredient) |
| (d) | Gafquat 755 in 20% strength aqueous solution | .75 g (0.15 g of active ingredient) |
| (e) | Copra-dimethylhydroxyethyl ammonium chloride in 30% strength aqueous solution | 2 g (0.5 g active ingredient) |

Similar results are found.

By placing one of the specified compositions in an aerosol container using 70% by weight of composition and 30% by weight of Freon (a 57:43 mixture of Freon 12 and Freon 114) similar results were obtained.

EXAMPLE 4

The following composition is prepared:

| | |
|---|---|
| Texapon WW 99 | 7 g |
| Vaseline oil | 15 g |
| Mirapol A15 (in 54% strength aqueous solution) | 7 g (3.4 g of active ingredient) |

-continued

| | |
|---|---|
| Antioxidant | |
| Preservative | |
| Jojoba oil q.s.p. | 100 g |

The hair washed with this "shampooing oil" is soft to the touch and easy to comb out.

EXAMPLE 5

The following composition is prepared:

| | |
|---|---|
| Zetesol 100 | 55.0 g |
| Polymer P1 in 60% strength aqueous solution | 5.7 g (3.4 g of active ingredient) |
| Perfume | |
| Vaseline oil q.s.p. | 100 g |

The hair washed with this "shampooing oil" is soft to the touch and easy to comb out.

EXAMPLE 6

The following composition is prepared:

| | |
|---|---|
| Texapon WW 99 | 35.0 g |
| Vaseline oil | 24.0 g |
| Ceraphyl 60 in 60% strength aqueous solution | 3.4 g (2.0 g of active ingredient) |
| Dyestuff | |
| Antioxidant | |
| Peanut oil q.s.p. | 100 g |

The hair washed with this "shampooing oil" is soft to the touch and easy to comb out.

EXAMPLE 7

The following composition is prepared:

| | |
|---|---|
| Zetesol 100 | 33.6 g |
| Lanoquat DES 50 at a concentration of 50% in 2-ethylhexane-1,3-diol | 4.0 g (2.0 g of active ingredient) |
| Vaseline oil | 24.0 g |
| Dyestuff | |
| Filter | |
| Antioxidant | |
| Water | 0.1 g |
| Peanut oil q.s.p. | 100 g |

This composition is applied to the hair after shampooing. After an application time of 15 minutes, rinsing and drying, it is found that the hair is soft to the touch and easy to comb out.

EXAMPLE 8

The following composition is prepared:

| | |
|---|---|
| Vaseline oil | 1.50 g |
| Colza oil | 3.50 g |
| Mirapol A 15 in 64% strength aqueous solution | 0.80 g (0.51 g of active ingredient) |
| Perfume | |
| Preservative | |
| Texapon WW 90 q.s.p. | 100 g |

This composition is used as a shampoo. After rinsing, it is found that the hair is soft to the touch and easy to comb out.

EXAMPLE 9

The following composition is prepared:

| | |
|---|---|
| Texapon WW 99 | 20 g |
| Mirapol A 15 in 64% strength aqueous solution | 0.80 g (0.52 g of active ingredient) |
| Perfume | |
| Antioxidant | |
| Preservative | |
| Cetiol HE q.s.p | 100 g |

EXAMPLE 10

The following composition is prepared:

| | |
|---|---|
| Zetesol 100 | 30 g |
| Vaseline oil | 38 g |
| Onamer M | 1.23 g (0.45 g of active ingredient) |
| Dyestuff | |
| Preservative | |
| Isopropyl myristate q.s.p. | 100 g |

The compositions of Examples 9 and 10 are applied under the conditions described in Example 1. The treated hair is soft to the touch and easy to comb out.

EXAMPLE 11

The following composition is prepared:

| | |
|---|---|
| Texapon WW 99 | 50 g |
| Oleyl alcohol | 32.20 g |
| Polymer P4 (in 45% strength aqueous solution | 1.13 g (0.5 g of active ingredient) |
| Perfume | |
| Dyestuff | |
| Antioxidant | |
| Olive oil q.s.p. | 100 g |

The hair treated with this "shampooing oil" is soft to the touch and easy to comb out.

EXAMPLE 12

The following composition is prepared:

| | |
|---|---|
| Texapon WW 99 | 34.0 g |
| Vaseline oil | 23.0 g |
| Polymer P1 (in 60% strength aqueous solution) | 2.7 g |
| Antioxidant (BHA/BHT) | 0.1 g |
| Perfume | 1.0 g |
| Preservative (Glydan) (containing 55% of active ingredient): 1,3-dimethylol-5,5-dimethylhydantoin | 0.2 g |
| Silica sold under the name Aerosil 130 by DEGUSSA | 6.0 g |
| Colza oil q.s.p. | 100.0 g |

This composition is applied to wet skin. After a contact time of a few minutes, the skin is rinsed under the shower.

It is found that the skin is soft to the touch.

EXAMPLE 13

The following composition is prepared:

| | |
|---|---|
| Monoamine ALX 100 | 20 g |
| Luviquat FC 905 at a concentration of | 1.25 g (that is |

-continued

| | |
|---|---|
| 40% in water | to say 0.5 g of active ingredient |
| Antioxidants | |
| Perfume | |
| Oleyl alcohol q.s.p. | 100 g |

20 ml of this composition are applied to wet clean hair after shampooing. After an application time of 10 minutes, the hair is rinsed with water. It is found that the hair is easy to comb out and soft to the touch in the wet state, and these properties of softness and ease of comb-out are retained in the dry state.

EXAMPLE 14

The following composition is prepared:

| | |
|---|---|
| TEXAPON WW 99 | 30 g |
| Vaseline oil | 25 g |
| LUVIQUAT FC 905 at a concentration of 40% in water | 1.25 g (that is to say 0.5 g of active ingredient) |
| Antioxidant | |
| Perfume | |
| Preservative | |
| Peanut oil q.s.p. | 100 g |

The procedure described in Example 13 is followed and similar results are found.

EXAMPLE 15

The following composition is prepared:

| | |
|---|---|
| AKYPOSAL 100 LFS | 25 g |
| Poly-(N—methyl-4-vinylpyridinium) iodide | 1 g |
| Water | 1 g |
| Antioxidant | |
| Preservative | |
| Oleyl alcohol q.s.p. | 100 g |

This composition is used as a shampoo.

This composition is applied to dry dirty hair. After an application time of 5 minutes, it is emulsified. The formation of a foam which is soft to the touch is observed.

After rinsing, the composition is applied to the hair again in order to carry out the second shampooing stage. After rinsing, the hair is soft to the touch and easy to comb out.

EXAMPLE 16

The following composition is prepared: Monoisopropanolamine salt of the following surface-active agent:

| | |
|---|---|
| R—O[CH$_2$—CH$_2$—O]$_n$—CH$_2$COO$^-$ with: n = 4 R = octylphenyl | 17.50 g |
| Oxyethyleneated C$_{12}$-C$_{14}$ alcohols (2 to 3 mols of ethylene oxide) | 3.75 g |
| Copra diethanolamide | 3.75 g |
| Vaseline oil | 25.00 g |
| Distearyldimethylammonium chloride | 2.00 g |
| Water | 0.10 g |
| Antioxidant | |
| Perfume | |
| Colza oil q.s.p. | 100 g |

This composition is used as a shampoo.
The procedure of Example 15 is followed and, after rinsing, this gives hair which is soft to the touch and easy to comb out in the wet state. In the dry state, the hair is soft, supple, shiny and also easy to comb out.

EXAMPLE 17

The following composition is prepared:

| | |
|---|---|
| AKYPOSAL 100 LFS | 9 g |
| Equimolar polycondensate of adipic acid and diethylenetriamine, crosslinked by a random oligomeric crosslinking agent prepared from epichlorohydrin, piperazine and sodium hydroxide, in the molar proportions (3/2/1), and described in French Application 77/06.031 of 2nd March 1977, in 10% strength aqueous solution | 5 g (that is to say 0.5 g of active ingredient) |
| Isopropyl myristate q.s.p. | 100 g |

EXAMPLE 18

The following composition is prepared:

| | |
|---|---|
| Monoisopropanolamine salt of sulphated oxyethyleneated lauryl alcohol at a concentration of 85% in ethanol | 6.0 g |
| LEXEIN CP 125 in aqueous solution containing 48% of active ingredient | 1 g (that is to say 0.5 g of active ingredient) |
| Oleyl alcohol q.s.p. | 100 g |

EXAMPLE 19

The following composition is prepared:

| | |
|---|---|
| Monoisopropanolamine salt of sulphated oxyethyleneated lauryl alcohol at a concentration of 85% in ethanol | 17 g |
| CARTARETINE F4 | 1 g (that is to say 0.5 g of active ingredient) |
| Isopropyl myristate q.s.p. | 100 g |

EXAMPLE 20

The following composition is prepared:

| | |
|---|---|
| Monoisopropanolamine salt of a mixture of polyoxyethyleneated carboxymethylated lauryl alcohol and polyoxyethyleneated carboxymethylated myristyl alcohol, of the formula: R—O[CH$_2$—CH$_2$—O]$_n$—CH$_2$COO$^-$ with: N = 4 R = C$_{12}$H$_{25}$/C$_{14}$H$_{29}$ | 17.50 g |
| Oxyethyleneated C$_{12}$/C$_{14}$ fatty alcohol 2 to 3 mols of ethylene oxide | 3.75 g |
| Copra diethanolamide | 3.75 g |
| Dimethyldistearylammonium chloride | 2 g |
| Water | 0.10 g |
| MIGLYOL 312 q.s.p. | 100 g |

EXAMPLE 21

The following composition is prepared: Monoisopropanolamine salt of the following surface-active agent:

| | |
|---|---|
| R—O[CH$_2$—CH$_2$—O]$_n$—CH$_2$COO$^-$ with: n = 4 | 100 g |

| | | |
|---|---|---|
| R = octylphenyl | | |
| CELQUAT L200 | 0.05 g | |
| Water | 2.45 g | |
| Isopropyl myristate q.s.p. | 100 g | |

The compositions of Examples 17 to 21 are used as shampoos. Similar results to those observed for the compositions of Examples 15 and 16 are found.

In the foregoing Examples, the various abbreviations or tradenames represent the following products:

Polymer P1

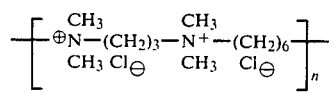

which can be prepared as described in French Patent Application No. 2,270,846.

MIRAPOL A 15

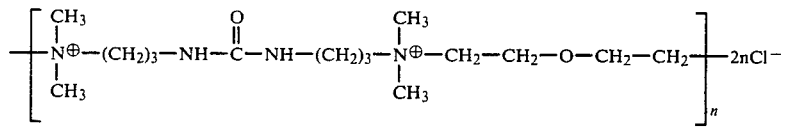

Poly-(N-(3-(dimethylammonio)-propyl)-N'-(ethyleneoxyethylenedimethylammoniopropyl)-urea dichloride) sold under the name MIRAPOL A 15 by MIRANOL.

| | |
|---|---|
| ONAMER M | Poly-(dimethylbutenylammonium chloride)-α,ω-bis-(triethanolammonium chloride) sold by ONYX |
| MERQUAT 100 | Dimethyldiallylammonium chloride homopolymer of molecular weight 100,000, sold by MERCK |
| POLYMER P2 | Cationic polycondensate of piperazine/diglycolamine/epichlorohydrin in the molar proportions of 4/1/5, described in Example 2 of French Patent 2,280,361 |
| POLYMER P3 | Polymer resulting from the polycondensation of equimolar amounts of adipic acid and diethylenetriamine, followed by crosslinking with epichlorohydrin (11 mols of epichlorohydrin per 100 amine groups) |
| GAFQUAT 755 | Quaternary polyvinylpyrrolidone copolymer having a molecular weight of 1,000,000, marketed by GENERAL ANILINE |
| POLYMER P4 | Polymer consisting of units of the formula: 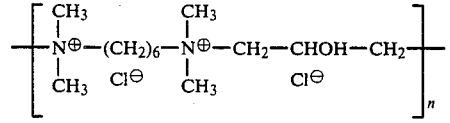 |
| TEXAPON WW 99 | Surface-active agent composed of the monoisopropanolamine salt of sulphated oxyethyleneated lauryl alcohol and of copra diethanolamide, sold by HENKEL |
| ZETESOL 100 | Surface-active agent composed of the isopropanolamine salt of sulphated oxyethyleneated lauryl alcohol and nonionics, sold by ZSCHIMMER & SCHWARZ |
| CETIOL HE | Glyceryl ester of coconut fatty acid, containing 7 mols of ethylene oxide, sold by HENKEL |
| LANOQUAT DES 50 | Quaternary lanoline of the formula: 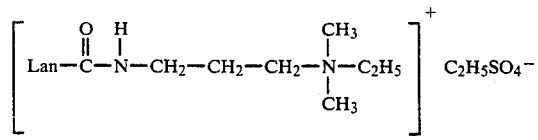 in which Lan denotes the acyl radicals derived from lanoline fatty acids, sold by MALSTROM |
| CERAPHYL 60 | α-Gluconamidopropyldimethyl-2-hydroxyethylammonium chloride sold by VAN DYK |
| MONOAMINE ALX 100 | Mixture of diethylamine dodecylbenzene |

| | -continued |
|---|---|
| | sulphonate and copra diethanolamide, marketed by MONA |
| LUVIQUAT FC 905 | Vinylimidazole (95%)/vinylpyrrolidone (5%) copolymer sold by B.A.S.F. |
| AKYPOSAL 100 LFS | Sulphated oxyethyleneated lauryl alcohol neutralised to the extent of 50% by diethylamine and 50% by monobutylamine, marketed by DSM |
| LEXEIN CP 125 | Cationic protein derived from collagen protein hydrolysate and from oleylamidopropyldimethylamine, sold by INOLEX |
| CARTARETINE F4 | Adipic acid/dimethylaminohydroxypropyldiethylenetriamine copolymer in 30% strength aqueous solution, sold by SANDOZ |
| MIGLYOL 812 | Triglyceride of saturated $C_8$-$C_{12}$ fatty acids derived from plants, sold by DYNA |
| CELQUAT L 200 | Cationic cellulose derivative sold by National Starch. |

The preservatives used in the foregoing examples are essentially chosen from amongst formaldehyde, 5-bromo-5-nitro-1,3-dioxane, sold under the name "Bronidox" by Henkel, and 1,3-dimethylol-5,5-dimethylhydantoin, sold under the name "Glydan".

We claim:

1. A single liquid phase oily and foamable composition suitable for application to keratin material and the skin comprising:
   (1) about 5 to 85% of an oil compound liquid at room temperature which is selected from the group consisting of mineral oil, animal oil, vegetable oil, synthetic oil, a triglyceride of a synthetic fatty acid, a fatty alcohol or an ester of a fatty acid and an alcohol;
   (2) an oil soluble surface active compound selected from the group consisting of (a) an anionic surface active agent, the acid group of which has been neutralized by an amine; (b) (a) above in combination with a non-ionic surface active agent; (c) (a) above in combination with an alkanolamide; and (d) (a) above in combination with a non-ionic surface agent and an alkanolamide;
   (3) about 0.05 to 10% of a cationic product; and
   (4) water in an amount equal to 5% or less by weight.

2. A composition according to claim 1 which contains 5 to 85% of at least one oily compound, 15 to 95% of at least one oil-soluble surface-active component, 0.05 to 10% of at least one cationic product and 0.1 to 5% of water, all by weight.

3. A composition according to claim 1 in which the mineral oil is liquid petrolatum, the animal oil is whale oil, seal oil, menhaden oil, halibut-liver oil, cod-liver oil, tuna oil, tallow oil, bovine oil, caballine oil, ovine oil, mink oil or otter oil, the vegetable oil is almond oil, peanut oil, wheatgerm oil, linseed oil, apricot kernel oil, nut oil, palm oil, pistachio oil, sesame oil, poppy oil, pine oil, castor oil, soya oil, avocado oil, safflower oil, coconut oil, hazelnut oil, olive oil, grapeseed oil, sunflower oil, colza oil, cade oil, maize germ oil, peach kernel oil, coffee bean oil or jojoba oil, the triglycerides of synthetic fatty acid is a triglyceride of caprylic and capric acids or of fatty acids having 6 to 12 carbon atoms, the fatty alcohol is oleyl alcohol or 2;1-octyldodecanol, and the fatty acid ester is an isopropyl ester of myristic acid, palmitic acid or stearic acid.

4. A composition according to claim 1 in which the anionic surface-active agent is a sulphated alkanol, sulphonated alkylbenzene, sulphated alkylpolyglycol ether, sulphated alkylphenol polyglycol ether, a carboxylated alkylpolyglycol ether or a carboxylated alkylphenol polyglycol ether, and the non-ionic surface-active agent is an alkyl polyglycol ether or an alkylphenol polyglycol ether.

5. A composition according to claim 1 in which the acid group of the anionic surface-active agent is neutralised by one or more of methylamine, ethylamine, diethylamine, propylamine, isopropylamine, butylamine or hexylamine, ethanolamine, diethanolamine, triethanolamine, propanolamine or mono-, di or tri-isopropanolamine, or dimethylaminoethanol, diethylaminoethanol, 2-amino-2-methylpropane-1,3-diol, aminomethylpropanol, N,N-dimethylisopropanolamine, N-propylethanolamine, N-propyldiethanolamine, N,N-diethylaminoethoxyethanol, monobutylethanolamine, tert.-butylethanolamine or tert.-butyldiethanolamine.

6. A composition according to claim 1 in which the oil-soluble surface-active component consists of:
   (1) 40 to 50% by weight of oxyethyleneated fatty alcohol having 10 to 18 carbon atoms, with 25 to 50% by weight of ethylene oxide,
   (2) 25 to 35% by weight of sulphated oxyethyleneated fatty alcohol as defined under (1), salified with an aliphatic amine or alkanolamine,
   (3) 10 to 20% by weight of alkanolamide, and
   (4) 5 to 15% by weight of sulphate or hydrochloride of an aliphatic amine or alkanolamine.

7. A composition according to claim 1 in which the cationic product is cationic polyamine, polyaminoamide or quaternary polyammonium polymer, the amine or ammonium group forming part of the polymer chain or being joined thereto.

8. A composition according to claim 1 in which the cationic product is a fatty amine salt, a quaternary ammonium salt, a quaternary halide of gluconamide, a cationic protein hydrolysate, a quaternary halide of mink oil amide, a quaternary derivative of dialkylaminopropylamide fatty halogenoalkanoate, a quaternary ammonium derivative of lanolin fatty acid, an alkylpyridinium salt or an imidazoline derivative.

9. A composition according to claim 1 in which the oily compound comprises 30 to 100% of liquid petrolatum and 0 to 70% of vegetable oil.

10. A composition according to claim 1 suitable for application to the hair or to the skin which contains one or more solvents other than water, preservatives, antioxidants, dyestuffs, perfumes, thickeners, opacifying agents or agents for imparting pearlescence.

11. A composition according to claim 1 which is in the form of an aerosol.

12. A single liquid phase oily and foamable composition suitable for application to keratin material and the skin comprising:
(1) about 5 to 85% of at least one oil compound liquid at room temperature which is selected from the group consisting of mineral oil, animal oil, vegetable oil, synthetic oil, a triglyceride of a synthetic fatty acid, a fatty alcohol and a fatty acid ester;
(2) about 15 to 95% of at least one oil soluble surface active compound selected from the group consisting of (a) an anionic surface active agent, the acid group of which has been neutralized by an amine; (b) (a) above in combination with a non-ionic surface active agent; (c) (a) above in combination with an alkanolamide; and (d) (a) above in combination with a non-ionic surface agent and an alkanolamide;
(3) a cationic product which is a cationic polyamine, a polyaminoamide or quaternary polyammonium polymer, the amine or ammonium group forming part of the polymer chain or being joined thereto, a fatty amine salt, a quaternary ammonium salt, a quaternary halide of gluconamide, a cationic protein hydrolysate, a quaternary halide of mink oil amide, a quaternary derivative of dialkylaminopropylamide fatty halogenoalkanoate, a quaternary ammonium derivative of lanolin fatty acid, an alkylpyridinium salt or an imidazoline derivative; and
(4) water in an amount equal to 5% or less by weight.

13. Process for the treatment of a keratin substance, which comprises applying thereto at least one composition as defined in claim 1, and rinsing the keratin substance after it has become impregnated by the composition.

14. Process according to claim 13 in which at least one said composition is applied to the hair before and and after shampooing, coloring, bleaching or perming or after shampooing, colouring, bleaching or perming.

15. Process according to claim 13 in which the said composition is applied to the skin following which it is rinsed off.

16. Process for the treatment of the hair which consists in washing it with a shampoo composition as defined in claim 1.

* * * * *